(12) United States Patent
Trudil et al.

(10) Patent No.: US 6,176,836 B1
(45) Date of Patent: Jan. 23, 2001

(54) BIOLOGICAL SAMPLE COLLECTION KIT

(76) Inventors: David Trudil, 12616 Mt. Laurel, Reisterstown, MD (US) 21136; Lawrence Loomis, 11374 Buckelberry Point, Columbia, MD (US) 21044

( * ) Notice: Under 35 U.S.C. 154(b), the term of this patent shall be extended for 0 days.

(21) Appl. No.: 09/160,153

(22) Filed: Sep. 25, 1998

(51) Int. Cl.[7] .................................................. A61B 10/00
(52) U.S. Cl. ........................ 600/572; 600/562; 600/573; 206/569; 206/363
(58) Field of Search .................................... 600/572, 573, 600/562; 422/50, 61; 435/4, 5, 30; 206/363, 438, 828, 223, 569, 570

(56) References Cited

U.S. PATENT DOCUMENTS

| | | | |
|---|---|---|---|
| 2,902,146 | * | 9/1959 | Doherty .............................. 206/63.2 |
| 4,078,656 | * | 3/1978 | Crane et al. ......................... 600/572 |
| 4,387,725 | * | 6/1983 | Mull .................................... 600/572 |
| 4,409,988 | * | 10/1983 | Greenspan ........................... 600/572 |
| 4,803,048 | * | 2/1989 | Nason .................................. 422/58 |
| 4,826,003 | * | 5/1989 | Levy .................................. 206/45.31 |
| 5,078,968 | * | 1/1992 | Nason .................................. 600/572 |
| 5,449,071 | * | 9/1995 | Levy .................................... 206/569 |
| 5,477,863 | * | 12/1995 | Grant ................................... 600/572 |
| 5,609,160 | * | 3/1997 | Bahl et al. ............................ 600/584 |
| 5,787,891 | * | 8/1998 | Sak ...................................... 600/572 |
| 5,910,122 | * | 6/1999 | D'Angelo ............................. 600/573 |
| 5,921,396 | * | 7/1999 | Brown, Jr. ........................... 206/569 |
| 5,931,303 | * | 8/1999 | Salvadori ............................. 206/570 |

\* cited by examiner

*Primary Examiner*—Cary O'Connor
*Assistant Examiner*—Charles Marmor, II
(74) *Attorney, Agent, or Firm*—Jonathan Grant; Grant Patent Services

(57) ABSTRACT

The present invention discloses a biological sample collection kit which can be utilized to collect samples of biological origin for use in any recovery and identification method. The biological sample collection kit comprises a sterile device for collecting a sample, a collection and dispersing device for depositing and holding the sample, a device for transferring the sample, and a container for storing the sample to be tested. There may also be a labeling system for identifying the sample and for diluting the sample. The biological sample collection kit preferably contains an outer bag which holds, in a sterile environment, all of the items used in the testing procedures. Additionally, a container of collection fluid is preferably included in the sample collection kit.

16 Claims, 1 Drawing Sheet

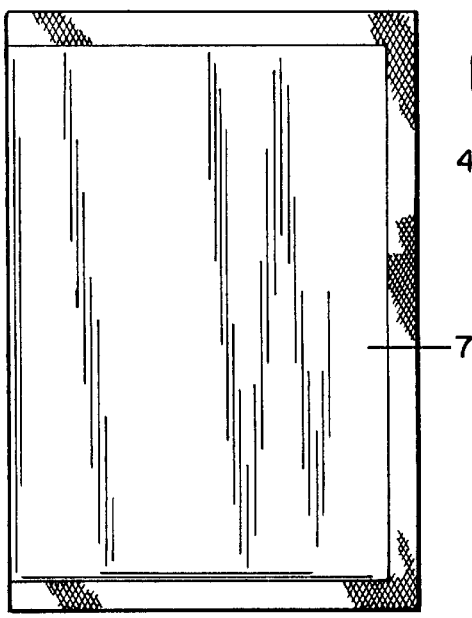
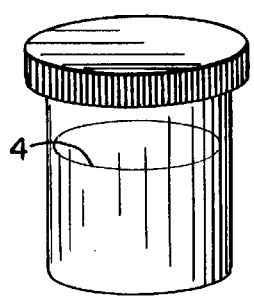
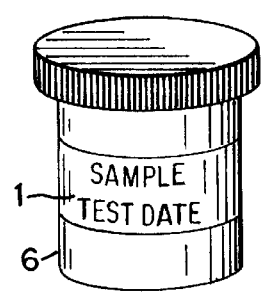
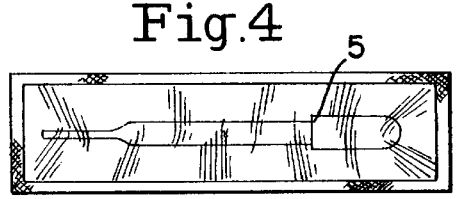
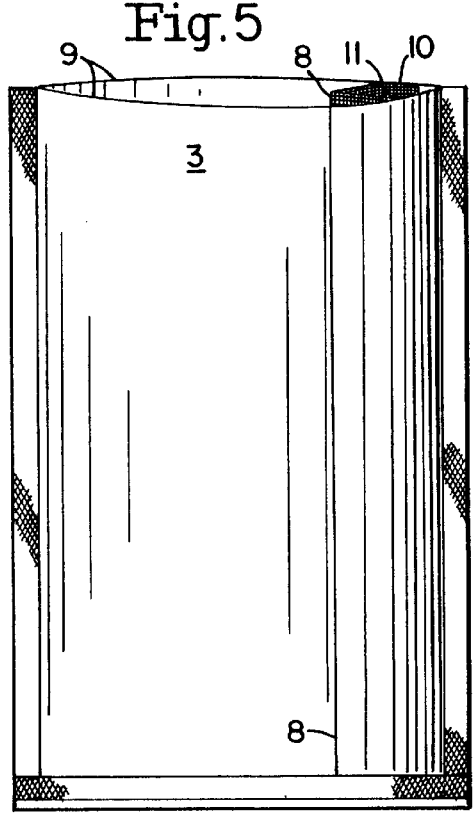
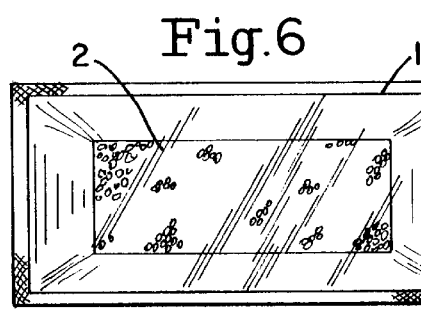
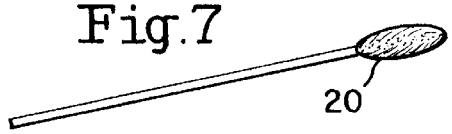
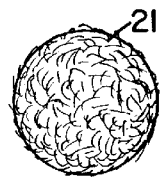

BIOLOGICAL SAMPLE COLLECTION KIT

BACKGROUND OF THE INVENTION

1. Field of the Invention

The present invention discloses a biological sample collection kit allowing for the collection and safe storing of samples.

2. Description of the Prior Art

Collection of microscopic biological samples has been random. For example, when a technician wants to test a surface for biological or chemical agents, he or she frequently has to search for a sterile cotton swab or cloth, wet it down if the surface is dry, and then wipe the surface. From there, a means must be found to transfer the absorbed material from the collection device (i.e., the cotton swab or cloth), to a storage place or an assay.

By not having all of the materials in one package which are necessary for collecting and testing the sample in one package, the risk of contamination of the sample and getting erroneous results is increased. Additionally, a great deal of time is wasted when the technician has to look around to find all of the collection and storage devices needed to safely collect and store a sample.

In the field, outside of the laboratory, it is even more necessary to have an efficient, light weight means of collecting and storing samples for testing in order to obtain more accurate results in a short period of time. A collection kit in the field must be self-contained as in the field, there is no lab supply cabinets or supply companies upon which to rely.

SUMMARY OF THE INVENTION

The present invention discloses a biological sample collection kit which can be utilized to collect samples of biological origin for use in any recovery and identification method. The identification method may be PCR, luimnescence, immunological, flow cytometry, etc.

The biological sample collection kit comprises a sterile means for collecting a sample, a means for depositing and holding the sample, a means for transferring the sample, and means for storing the storing the sample to be tested. There may also be means for identifying the sample and for diluting the sample. The biological sample collection kit preferably contains an outer bag which holds, in a sterile environment, all of the items used in the testing procedures. Additionally, a container of collection fluid is preferably included in the sample collection kit.

BRIEF DESCRIPTION OF THE DRAWINGS

FIG. 1 is a perspective view of the storage bag,

FIG. 2 is a perspective view of a collection fluid container;

FIG. 3 is a perspective view of a sample collection container;

FIG. 4 is a perspective view of a sterile pipette;

FIG. 5 is a perspective view of a filtered bag;

FIG. 6 is a perspective view of a sponge;

FIG. 7 is a perspective view of a swab; and

FIG. 8 is a perspective view of a cotton swab.

DETAILED DESCRIPTION OF THE INVENTION

The sample collection kit preferably contains a sponge 2, a filtered bag 3, a buffer solution 4, a pipette 5, and a specimen collection. vial 6. In a preferred embodiment of the invention, these items are kept in a collection kit bag 7. The collection kit bag 7 is preferably a sealed bag, which is preferably hermetically sealed, and sterile inside the bag. The bag may be made out of a metal foil, or a plastic.

The sponge 2 is preferably sterile, and kept in a bag or sealed container 12, preferably a stomacher bag. The sponge 2 will be removed from the bag 12 just prior to use. The sterile sponge 2 is used to wipe surfaces to be tested for bacteria, chemicals or other foreign matter from a surface area. If the area to be tested is dry, the sponge 2 may be first hydrated with the buffer solution 4. The buffer solution may be a carbonate, phosphate, or any other appropriate buffer.

In another embodiment of the invention, a sterile swab 20 is used in place of the sponge. Similarly, a sterile cotton ball 21 may be used, or any other absorbent material.

The filtered bag 3 is preferably a stomacher bag 3, with the bag having a filter 8 within said bag. This filter 8 may be a porous plastic or a paper filter, adhered to the walls 9 of the bag 3, with an opening 10 at the top of the bag, and preferably cylindrical in shape. The filter 8 preferably runs the length of the bag, with the filter 8 being attached to the front and back of the bag.

In place of the bag, any sterile receptacle may be used. However, a plastic sterile bag, with a filter and a stomacher bag, is preferred.

After the sponge 2 is used to wipe down a surface area to be tested, it is placed in a general part of the filtered bag 3. After the sponge is placed in the filter bag 3, it is squeezed through the filter bag 3. That is, the user squeezes the filter bag 3 with the sponge 2 inside the filter bag 3. If so desired, additional buffer solution 4 may be added to the general part of the filtered bag 3. It is best that the filtered bag be gently shaken to mix the contents A pipette 5 or syringe, preferably a sterile transfer pipette contained in a bag or sealed container 12 until use, is inserted into the opening of the filter compartment 11. The filter serves the purpose of keeping out any large, extraneous material from the fluid to be tested, but which the sponge 2 may have picked up from the testing area, including paint chips, dust, wood chips, etc.

The sample is drawn up into the pipette 5. From there, the sample may be placed in a collection vial 6, or the sample may be directly assayed. Labels 1 included in the kit may be attached to the collection tube properly identify the sample.

Many modifications and variations of the present invention are possible in light of the above teachings. It is, therefore, to be understood within the scope of the appended claims the invention may be protected otherwise than as specifically described.

What is claimed is:

1. A sample collection kit comprising:
   at least one sterile absorbent collection device for collecting a sample;
   at least one deposit and holding container for depositing and holding the sample, said at least one deposit and holding container being a sterile filtered bag;
   at least one sample transferor for transferring the sample;
   at least one sample storer for storing the sample to be tested;
   a container for holding said at least one collection device, said at least one deposit and holding container, and said at least one sample storer; and
   at least one device for identifying the sample.

2. The sample collection kit of claim 1, further comprising means for identifying the sample and means for diluting the sample.

3. The sample collection kit of claim 1, wherein said at least one sterile absorbent collection device is selected from the group consisting of at least one sponge, a swab, and a cotton ball.

4. The sample collection kit of claim 1, wherein said at least one sterile filtered bag is a plastic bag.

5. The sample collection kit of claim 1, wherein said sample transferor is at least one sterile pipette.

6. The sample collection kit of claim 1, wherein said sample storer to be tested is at least one collection tube.

7. The sample collection kit of claim 6, wherein said at least one collection tube is at least one plastic screw top tube.

8. The sample collection kit of claim 6, wherein said at least one collection tube is at least one sealable vial.

9. The sample collection kit of claim 1, wherein said at least one device for identifying the samples are labels.

10. A sample collection kit comprising:
    at least one sterile sponge for collecting a sample, at least one filtered bag for storing said sample after it has been collected, at least one collection vial for storing said sample after it has been removed from the filtered bag, at least one sterile pipette for transferring the sample from the filtered stomacher bag to said collection vial, collection fluid stored in at least one vial, and a sterile container for holding said at least one sterile sponge, said at least one filtered bag, said at least one collection vial, said at least one sterile pipette, and the collection fluid stored in said at least one vial.

11. The sample collection kit of claim 10, further comprising at least one sterile bag for storing said at least one sterile sponge.

12. The sample collection kit of claim 10, further comprising at least one sterile package for storing said at least one sterile pipette until use.

13. The sample collection kit of claim 10, further comprising said at least one label to attach to said at least one collection vial.

14. A sample collection kit comprising:
    at least one sterile absorbent device for collecting a sample;
    at least one filtered bag for storing said sample after it has been collected; said filtered bag comprising a filter adhered to the walls of the bag, with an opening at the top of the bag, said filter running the length of the bag;
    at least one collection vial for storing said sample after it has been removed from the filtered bag;
    at least one sterile pipette for transferring the sample from the filtered bag to said collection vial,
    collection fluid stored in at least one vial; and
    a sterile container for holding said at least one sterile device, said at least one filtered bag, said at least one collection vial, said at least one sterile pipette, and the collection fluid stored in said at least one vial.

15. The sample collection kit of claim 14, further comprising labels, to label said vials.

16. The sample collection kit of claim 14, wherein said filter of said filtered bag is made of a material selected from the group consisting of porous plastic and paper filter, cylindrical in shape.

* * * * *